United States Patent [19]
Alles

[11] Patent Number: 4,887,999
[45] Date of Patent: Dec. 19, 1989

[54] SINGLE USE-DISPOSABLE HYPODERMIC SYRINGE

[75] Inventor: Anthony Alles, Ottawa, Canada

[73] Assignee: Syntrall Canada Inc., Ottawa, Canada

[21] Appl. No.: 186,469

[22] Filed: Apr. 26, 1988

[51] Int. Cl.⁴ .............................................. A61M 5/00
[52] U.S. Cl. ..................................... 604/110; 604/208
[58] Field of Search ............... 604/110, 224, 218, 208, 604/209, 210, 228

[56] References Cited

U.S. PATENT DOCUMENTS

| 3,890,971 | 6/1975 | Leeson et al. | 604/110 |
| 3,949,748 | 4/1976 | Malmin . | |
| 4,233,975 | 11/1980 | Yerman . | |
| 4,246,898 | 1/1981 | Travalent et al. . | |
| 4,275,729 | 6/1981 | Silver et al. . | |
| 4,300,678 | 11/1981 | Gyure et al. | 604/263 |
| 4,367,738 | 1/1983 | Legendre et al. | 604/218 |
| 4,493,703 | 1/1985 | Butterfield . | |
| 4,562,844 | 1/1986 | Carpenter et al. . | |
| 4,650,468 | 3/1987 | Jennings, Jr. . | |
| 4,775,364 | 10/1988 | Alles . | |

FOREIGN PATENT DOCUMENTS 711528  6/1965 Canada .
1144838  4/1983 Canada .
1147627  6/1983 Canada .
1195895 10/1985 Canada .

Primary Examiner—John D. Yasko
Attorney, Agent, or Firm—Burns, Doane, Swecker & Mathis

[57] ABSTRACT

There is described a single use disposable hypodermic syringe and a manner for its manufacture. The syringe has a polystyrene barrel and a plunger assembly snuggly mounted for reciprocation therein. A plunger movement-limiting means is provided and comprises a first ratchet-like track section extending longitudinally of the barrel on its inside wall, a second ratchet-like track section parallel to and spaced from the first track section and oriented in a direction opposite to the first track, and a cross-over ratchet-like track section connecting the first and second track sections, and track engaging click means on the plunger assembly. The plunger assembly may be, moved outwardly of the barrel unidirectionally along the first track section to perform a syringe priming stroke; relocated within the barrel unidirectionally along the cross-over track section to the second track; and moved inwardly of the barrel unidirectionally along the second track section, to perform a delivery stroke.

10 Claims, 2 Drawing Sheets

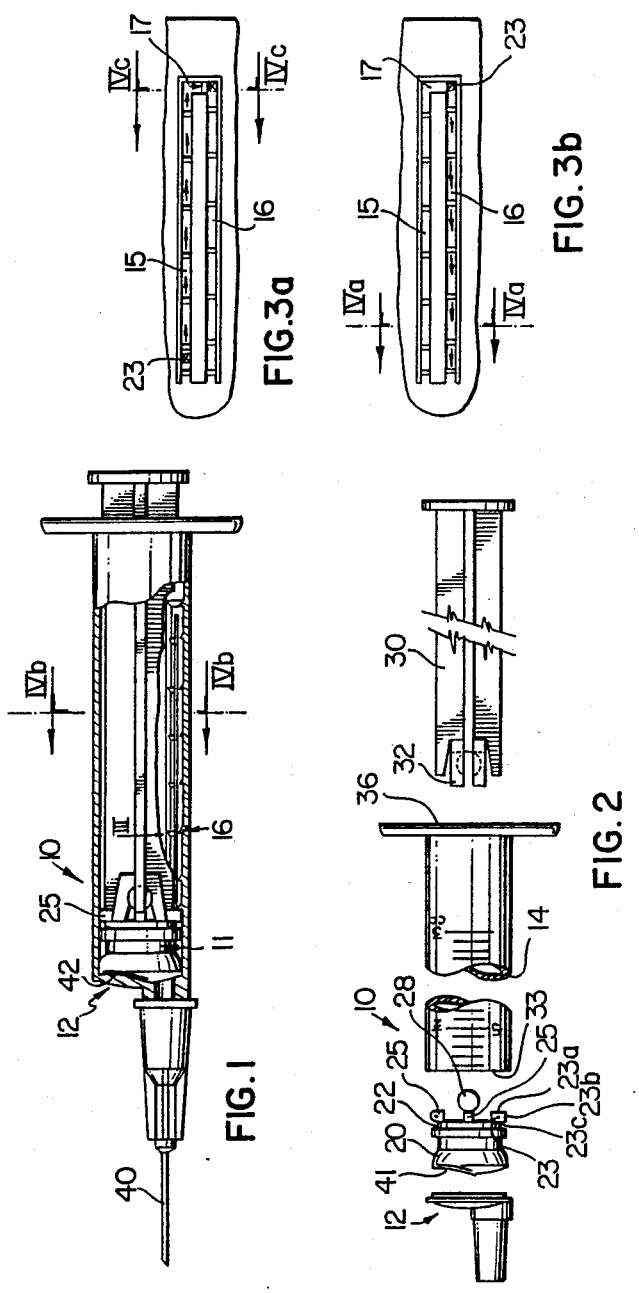

SINGLE USE-DISPOSABLE HYPODERMIC SYRINGE

BACKGROUND OF THE INVENTION

The present invention relates to single use disposable hypodermic syringes of uncomplicated construction to enable low cost mass production.

With the current medical knowledge of the danger of transmitting disease by use of un-hygenic hypodermic syringes, considerable efforts have been taken to provide a disposable syringe which after use is rendered inoperable and consequently cannot be used for a second time.

One set of proposals has been to provide a lance-like member on the leading edge of the hypodermic piston plunger so that on delivery of medication the lance pierces the front end wall of the syringe, thus rendering the syringe useless.

Another set of proposals has been to introduce a capturing chamber at the front end of the inside of the syringe barrel such that on delivery of medication the syringe piston is trapped within the barrel and any attempt to retract the piston causes the syringe to fail structurally and become unusable.

A third proposal, for use with cartridge packaged medication, has been to render the drive piston of the syringe non-retractable by including on it a resilient disc-like element or, in another such proposal, a plurality of short, stiff, flexible spikes are attached to the piston so as to project outwardly at an oblique angle and engage the inside of the tubular body of the syringe and allow very little retraction of the piston.

All the previous proposals have had limitations in that they are either workable only with cartridge loaded or pre-filled syringes, or could be subject to some form of tampering.

A major drawback with all non-cartridge type syringes is that they have not been "auto-distruct" at the beginning of the delivery stroke.

SUMMARY OF THE INVENTION

The present invention seeks to provide a single use, disposable hypodermic syringe that cannot be reused or reloaded and once primed is capable of one delivery stroke only, and which overcomes the drawbacks of prior proposals.

According to the present invention there is provided in a disposable hypodermic syringe having a barrel and a plunger assembly snuggly mounted for reciprocation therein, a plunger movement-limiting means comprising a ratchet-like track and co-operating click means located on one or another of an inside surface of said barrel and said plunger assembly and operable to permit the plunger, on engagement of said click means with a first section of track, to move unidirectionally to perform a priming stroke and, on engagement of said click means with a second section of track, to move unidirectionally to perform a delivery stroke.

Preferably locating means is positioned between the plunger assembly and the barrel inside surface to permit the snug mounting of the plunger assembly in the barrel and to urge the click means to engage the ratchet-like track.

According to a preferred feature of the invention there is provided in a disposable hypodermic syringe having a barrel and a plunger assembly snuggly mounted for reciprocation therein a plunger movement limiting means comprising a first ratchet-like track section extending longitudinally of the barrel on an inside wall thereof, a second ratchet-like track section on the wall parallel to and spaced from the first track section and oriented in a direction opposite thereto, a cross-over ratchet-like track section connecting the first and second track sections, and track engaging click means on the plunger assembly whereby the plunger assembly may be, (a) moved outwardly of the barrel unidirectionally along the first track section to perform a syringe priming stroke;

(b) relocated within the barrel unidirectionally along the cross-over track section to the second track; and (c) moved inwardly of the barrel unidirectionally along the second track section to perform a delivery stroke.

Preferably the click means has contact faces located substantially at right angles to one another for engaging said first and cross-over cross-sections.

In a preferred construction the plunger assembly comprises a plunger tip, a tip retaining member for receiving the tip, a plunger rod, and frangible connections between the plunger rod and the tip retaining member. Conveniently the frangible connections may comprise a ball member extending longitudinally from the tip retaining member and a co-operating ball member receiving and retaining member on the plunger rod.

According to one preferred feature of the invention the click means and three locating members may be arranged at equal angular spacings about, and extending outwardly of, the tip retaining member.

The invention also envisages a method of assembling a hypodermic syringe having a tubular barrel opened at both ends and a plunger assembly, the barrel having opposite sense first and second ratchet-like track sections extending longitudinally of and parallel to each other on the inside wall of the barrel and connected by a cross-over ratchet-like track section; the plunger assembly comprising a plunger tip, a tip retaining member and a plunger rod and means to frangibly connect the tip retaining member and the plunger rod, which connecting means comprise a ball member extending longitudinally from the tip retaining member and a co-operating ball receiving and retaining member on the plunger rod; a ratchet-like track section engaging click means, and barrel inside wall engaging locating members extending from said tip retaining member; and a needle receiving end cap for closing a front end of the tubular barrel, which method comprising the steps of assembling the plunger tip and tip retaining means into a subassembly, introducing the sub-assembly into the barrel through its front end, engaging an inwardly directed first ratchet-like track section with said click means and the barrel inside wall with said locating members to capture said sub-assembly in the barrel, inserting the plunger rod into the tubular barrel from the back end thereof until the ball member and its receiving and retaining member engage and lock, and permanently attaching the end cap to seal the front end of the barrel.

According to a feature of the invention the barrel, including its leading end cap is made from polystyrene.

BRIEF DESCRIPTION OF THE DRAWINGS

The following is description by way of example of one embodiment of the present invention reference being had to the accompanying drawings in which:

FIG. 1 is a general assembly view of the hypodermic syringe, shown partially in section;

FIG. 2 is an exploded view of the syringe shown in FIG. 1, as the syringe undergoes assembly;

FIGS. 3a and 3b are views of the track sections on the inside wall of the barrel of the syringe as looked at in the direction of the arrow III in FIG. 1 but shown with the curvature of the wall flattened out;

DESCRIPTION OF THE PREFERRED EMBODIMENTS

Turning now to the drawings, a hypodermic syringe 10 has a plunger assembly 11 and a hypodermic needle accommodating end cap 12.

Figure 4A:
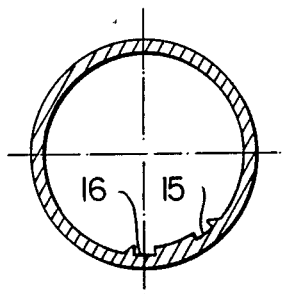
FIGS. 4a, 4b and 4c are sections taken along the lines IVa and IVb and IVc in FIGS. 3b, 1 and FIG. 3a respectively.
Figure 4B:
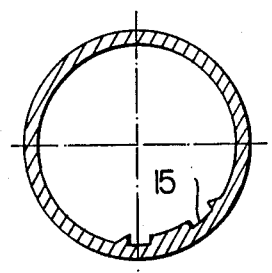
Figure 4C:
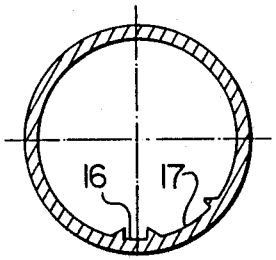
Figure 5B:
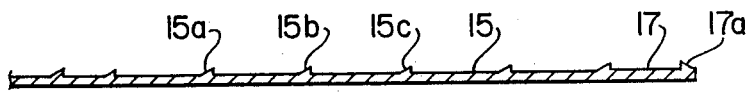
FIGS. 5a and 5b are sections through the barrel wall showing the unidirectional ratchet-like track profiles for the delivery and priming strokes.
Figure 5A:
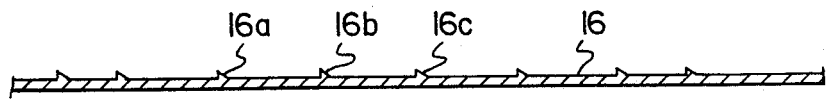

The hypodermic syringe 10 has a hollow barrel 14, preferably made from polystyrene which carries on its inside wall a pair of longitudinally extending parallel ratchet-like track sections 15 and 16 (see particularly FIGS. 3a, 3b). The tracks 15 and 16 are arranged in opposite senses, that is to say the track 15 is arranged with its teeth 15a, 15b, 15c, etc. to have a sloping face on one side and a locking face on the other side so as to be unidirectionally oriented inwardly of the syringe barrel. On the other hand the track 16 is unidirectionally sensed outwardly of the syringe barrel by having its sloping locking faces 16a, 16b, 16c, etc. arranged in the opposite direction. The tracks 15 and 16 are connected at the inner end by a cross-over track 17 which is also of ratchet-like configuration and having a tooth 17a (FIG. 5b) arranged in the opposite direction to teeth 15a, 15b, 15c, etc. to provide an end to the track 15. The other teeth in the cross-over section 17 are shown diagrammatically in FIGS. 3a and 3b and are sensed in a direction from first track section 15 to second track section 16.

Referring again to FIGS. 1 and 2 the plunger assembly which fits into barrel 14 comprises a plunger tip 20, conveniently manufactured from compressable vinyl rubber which is received and sits on the tip retainer member 22 which forms a sub-assembly with it.

A track engaging plastic material click 23 resiliently depends from the member 22. The click 23 is preferably of square cross-section. Three round nosed locating members 25 are spaced, together with the click member 23, uniformly circumferentially around the retaining member 22 at 90° intervals and slightly project resiliently from the member 22. The locating members 25 are urged outwardly so as to engage the inside surface of the barrel 14. Extending outwardly of the tip retaining member along its longitudinal axis, on a stem is a ball 28.

The piston plunger 30 is of cruciform configuration and terminates inwardly with a ball receiving and retaining member 32.

During assembly of the hypodermic syringe the sub-assembly of plunger tip 20 and plunger tip retaining member 22 is first assembled into the sub-assembly which is then introduced into the front 33 of the barrel 14 with the click 23 engaging in the ratchet-like track 15 and the locating members 25 pressing against the inner walls of the barrel 14 to maintain the click 25 in engagement with the ratchet-like track 15. Thus, the sub-assembly is captured in the barrel of the syringe against removal outwardly. The plunger piston 30 is then inserted into the rear end 36 of the syringe and pushed inwardly until the member 32 is forced apart by the ball 28 and then springs closed upon it to capture the ball 28 in the member 32 and thus attach the piston 30 to the member 22. The assembly of the syringe is completed by permanently cementing cap 12, again preferably of polystyrene to the open end 33. The hypodermic needle 40 is precemented into cap 12. It has been found that by making the barrel 14 and its cap 12 from polystyrene, an unexpectedly effacious syringe is obtained.

OPERATION

When it is desired to use the syringe, it is removed from its sterile packaging and the needle 40 inserted into a phial of medication. The syringe then is primed by pulling the plunger 30 outwardly of the barrel, with the click 23 running in the track 15 and engaging the track with its rearwardly directed face 23a. When the syringe is fully primed, the face 23a of the click 23 will encounter the tooth 17a of the cross-over track 17 and at this position the plunger can be neither retracted further nor advanced (it will be understood that the spacing of the teeth 15a, 15b, 15c is illustrative only and in fact the teeth are so close together that essentially no forward motion of the plunger is possible once the syringe has been charged). By rotating the plunger 30 clockwise the face 23b of the click moves unidirectionally across the ratchet-like track 17 from the track 15 to the track 16. Because of the orientation of the teeth in the track 17 it is not possible to return the click to the track 15. The twisting motion is continued until the click 23 engages in the track 16 with its leading face 23c. Now it is possible to perform the medication delivery stroke by pushing the plunger 30 forwardly into the barrel of the syringe with the click 23 running along the track 16. Again the spacing of the teeth 16a, 16b and 16c in the track 16, is such that it is impossible to again withdraw the plunger assembly from the syringe barrel and on completion of delivery it is impossible to again recharge the syringe.

If an operator attempts to forceably overcome the action of the click and the teeth of the track 16 the only result would be to cause the frangible connection provided by the ball 28 and its retainer 32, to sever.

It will be understood that other modifications are permissible within the scope of the invention, for example a suction cup 41 could be provided on the plunger tip 20 to co-operate with a suction pad 42 on the inner wall of the cap 12 (see FIG. 1). But provided that the form of the ratchet-like track 16 and the strength of the click 23 have been properly selected it is likely to be unnecessary to provide it as modification.

Again while the track has been shown on the inside wall of the barrel and the click has been shown on the plunger assembly, conceivably the locations could be reversed, as could those of the locating members.

What I claim as my invention:

1. In a disposable hypodermic syringe having a barrel and a plunger assembly snugly mounted for reciprocation therein, a plunger movement-limiting means comprising a ratchet-like track and co-operating click means located one on an inside surface of said barrel and the other on said plunger assembly and operable to permit the plunger, on engagement of said click means with a first section of track, to move unidirectionally to perform a priming stroke and, on engagement of said click means with a second section of track, to move unidirectionally to perform a delivery stroke.

2. A disposable hypodermic syringe as claimed in claim 1 in which locating means is positioned between said plunger assembly and said barrel inside surface to provide the snug mounting and urge said click means to engage said ratchet-like track.

3. In a disposable hypodermic syringe having a barrel and a plunger assembly snuggly mounted for reciprocation therein, a plunger movement-limiting means comprising a first ratchet-like track section extending longitudinally of said barrel on an inside wall thereof, a second ratchet-like track section parallel to and spaced from said first track section and oriented in a direction opposite thereto, a cross-over ratchet-like track section connecting said first and second track sections, and track engaging click means on said plunger assembly whereby the plunger assembly may be,
 (a) moved outwardly of said barrel unidirectionally along said first track section to perform a syringe printing stroke;
 (b) relocated within said barrel unidirectionally along said cross-over track section to said second track; and
 (c) moved inwardly of said barrel unidirectionally along said second track section, to perform a delivery stroke.

4. A disposable hypodermic syringe as claimed in claim 3 in which said plunger assembly is snuggly mounted in said barrel by the action of locating members circumferentially spaced about said plunger assembly in friction contact with said barrel inside wall whereby to urge said click means into engagement with said ratchet-like track.

5. A syringe as claimed in claim 4 in which three locating members are uniformly angularly spaced around said plunger assembly about said click-means and resiliently urged into friction contact with said barrel inside walls.

6. A syringe as claimed in claim 3 in which said click means has contact faces located substantially at right angles to one another for engaging said first and cross-over track sections.

7. A syringe as claimed in claim 1 in which said plunger assembly comprising a plunger tip, a tip retaining member for receiving said tip, a plunger rod and frangible connections between said plunger rod and said tip retaining member.

8. A syringe as claimed in claim 7 in which said frangible connections comprise a ball member extending longitudinally from said tip retaining member and a co-operating ball member receiving and retaining member on said plunger rod.

9. A syringe as claimed in claim 7 in which said click means and three locating members are arranged at equal angular spacings about, and extending outwardly of, said tip retaining member.

10. A method of assembling a hypodermic syringe having a tubular barrel open at both ends and a plunger assembly, said barrel having opposite sense first and second ratchet-like track sections extending longitudinally of and parallel to each other on the inside wall of the barrel and connected by a cross-over ratchet-like track section; said plunger assembly comprising a plunger tip, a tip retaining member, a plunger rod and means to frangibly connect said tip retaining member and said plunger rod, which connecting means comprise a ball member extending longitudinally from the top retaining member and a co-operating ball member receiving and retaining member on said plunger rod; a ratchet-like track section engaging click means, and barrel inside wall engaging location members, extending from said tip retaining member; and a needle receiving end cap for closing a front end of said tubular barrel, which method comprises the steps of assembling said plunger tip and tip retaining means into a sub-assembly, introducing said sub-assembly into the barrel through its front end, engaging an inwardly directed first ratchet-like track section with said click means and the barrel inside wall with said locating members to capture said subassembly in said barrel, inserting said plunger rod into said tubular barrel from the back end thereof until said ball member and its receiving and retaining member engage and lock, and permanently attaching said end cap to seal said front end of said barrel.

* * * * *